United States Patent [19]

Okamoto et al.

[11] Patent Number: 5,306,714

[45] Date of Patent: Apr. 26, 1994

[54] (S)-2,3-DIHYDROPOLYPRENYL, MONOPHOSPHATE, AND AGENTS FOR INHIBITING THE METASTASIS OF CANCERS

[75] Inventors: Yasushi Okamoto, Tokyo; Masahiro Tsuji, Kawagoe; Hiroyuki Yamazaki, Fujimi, all of Japan

[73] Assignee: Nisshin Flour Milling Co., Ltd., Tokyo, Japan

[21] Appl. No.: 79,271

[22] Filed: Jun. 21, 1993

[30] Foreign Application Priority Data

Aug. 17, 1992 [JP] Japan .................................. 4-217882
Mar. 29, 1993 [JP] Japan .................................. 5-069750

[51] Int. Cl.$^5$ ...................... A61K 31/66; C07F 9/113
[52] U.S. Cl. ..................................... 514/134; 558/213
[58] Field of Search .......................... 558/213; 514/134

[56] References Cited

U.S. PATENT DOCUMENTS 5,004,735  4/1991  Okamoto et al. .................... 514/134

FOREIGN PATENT DOCUMENTS

| 0350801 | 1/1990 | European Pat. Off. |
|---------|--------|--------------------|
| 2569108 | 2/1986 | France . |
| 2-11513 | 1/1990 | Japan . |
| 2-25415 | 1/1990 | Japan . |
| 4-52251 | 8/1992 | Japan . |

OTHER PUBLICATIONS

Chemical Abstracts, vol. 106, No. 7, Feb. 16, 1987, AN 46268d, P. Loew, et al., "Effectivity of Dolichyl Phosphates with Different Chain Lengths as Acceptors of Nucleotide Activated Sugars", p. 285.

Chemical Abstracts, vol. 103, No. 15, Oct. 14, 1985, AN 118321, P. Loew, et al., "Reaction of Optically Active S-and R-Forms of Dolichyl Phosphates with Activated Sugars", p. 277.

Cancer Letters, 57 (1991), pp. 159-163, Y. Okamoto, et al., "Inhibition of Growth and Pulmonary Metastasis of B16-F10 Murine Milanoma by N-1554, A Polyprenyl Phosphate".

*Primary Examiner*—Mary C. Lee
*Assistant Examiner*—Michael G. Ambrose
*Attorney, Agent, or Firm*—Oblon, Spivak, McClelland, Maier & Neustadt

[57] ABSTRACT

Disclosed are (S)-2,3-dihydropolyprenol of formula (I)

[Chemical structure I]

wherein m is 7 or 8 and (S)-2,3-dihydropolyprenyl monophosphate of formula (II)

[Chemical structure II]

wherein m is 7 or 8 as well as pharmaceutically acceptable salts thereof. They are useful as a medicament for inhibiting the growth and/or metastasis of cancers.

2 Claims, No Drawings

(S)-2,3-DIHYDROPOLYPRENYL, MONOPHOSPHATE, AND AGENTS FOR INHIBITING THE METASTASIS OF CANCERS

FIELD OF THE INVENTION

This invention relates to new (S)-2,3-dihydropolyprenols, new (S)-2,3-dihydropolyprenyl monophosphates, pharmaceutically acceptable salts thereof, processes of preparing the same and agents for inhibiting the growth and/or metastasis of cancers.

BACKGROUND OF THE INVENTION

In our country, cancers are the first of death causes among various diseases. Further, recent statistics show that the number of deaths from cancers is yearly increasing. There are a variety of views about its cause, but it has been desired to establish at once a new method for the treatment of cancers.

A variety of methods for the treatment of cancers have hitherto been attempted, including surgical operation, radiotherapy and chemotherapy, alone or in combination. In particular, surgical operation is highly effective in the removal of primary cancers, but it is inoperative for inoperable organ cancers and cancers in which a tumor metastasis is initiating. Radiotherapy and chemotherapy are often applied to inoperable primary cancers in organs or metastatic cancers. However, they have a tendency to injure a normal cell, which results in appearance of undesirable side effects such as reduction of immunological, metabolic and hematogenous functions, thus the scope of the application being limited. Even if growth of cancers in the specific region of the body is successfully inhibited by such radiotherapy or chemotherapy, growth of metastatic cancers in other regions may often lead to death of the patient.

Many reports state that the racemate, 2,3-dihydropolyprenol compounds have low side effects to an organism with the activities for suppressing the growth and metastasis of cancers (Japanese Patent Kokoku Hei 4-52251, Japanese Patent Kokai Hei 2-11513, Japanese Patent Kokai Hei 2-25415, Cancer Letters, 1991, vol. 57, 159-163). However, those compounds are not satisfactory for therapeutic agents for cancers.

Under such circumstances, there is a continuing desire to develop compounds having lower side effects to an organism and more potent inhibitory activities against the growth or metastasis of cancers than prior compounds.

DISCLOSURE OF THE INVENTION

The present invention provides in one aspect a (S)-2,3-dihydropolyprenol of formula (I)

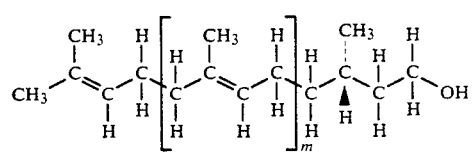

wherein m is 7 or 8 and a (S)-2,3-dihydropolyprenyl monophosphate of formula (II)

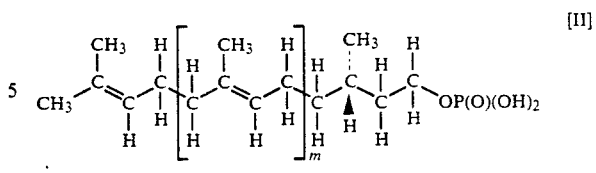

wherein m is 7 or 8 as well as the pharmaceutically acceptable salts thereof.

The invention provides in another aspect a process of preparing a (S)-2,3-dihydropolyprenol of formula (I)

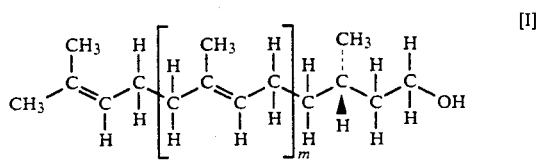

wherein m is 7 or 8, which comprises asymmetrically reducing a polyprenol of formula (III) at the double bond at the 2-position of the polyprenol

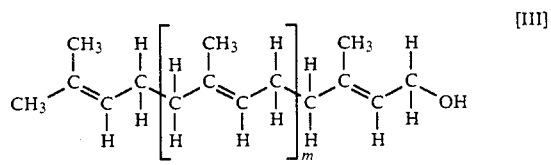

wherein m is 7 or 8.

The asymmetric reduction can use any reaction reagents capable of selectively reducing the double bond at the 2-position of the polyprenol. For instance, the asymmetric reduction includes the reaction using as a catalyst an asymmetric ruthenium-phosphine complex in a stream of hydrogen. The asymmetric ruthenium-phosphine complex includes Ru((R)-BINAP)(O$_2$Ct-Bu)$_2$, Ru((R)-BINAP)(O$_2$CPh)$_2$, Ru((R)-BINAP)(O$_2$CCH$_3$), Ru((R)-BINAP)(O$_2$CCF$_3$) and the like, the latter two compounds being preferred. A molar ratio of the catalyst to the polyprenol ranges from 1/100 to 1/50000. The hydrogen pressure ranges from 20 atms. to 150 atms. The reaction is carried out at a temperature in the ragne of room temperature to 100° C., room temperature being preferable. The solvents which can be used in the reaction include an alcohol solvent such as methanol, ethanol and a mixed solvent of the alcohol solvent with a halogen solvent such as methylene chloride, chloroform.

The invention provides in a further aspect a process of preparing a (S)-2,3-dihydropolyprenyl monophosphate of formula (II)

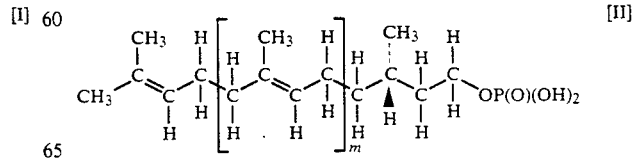

which comprises subjecting to phosphorylation, a (S)-2,3-dihydropolyprenol of formula (I)

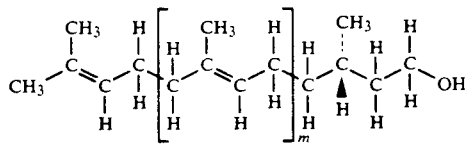

The phosphorylation can be carried out in a conventional manner, for example by reacting the (S)-2,3-dihydropolyprenol with phosphorus oxychloride in the presence of pyridine followed by partial hydrolysis of the reaction product. In the reaction of said polyprenol with phosphorus oxychloride to form an intermediate, dichlorophosphate, basic compounds may be used including trimethylamine, triethylamine, pyridine or the like. The solvents which can be used in the reaction include an ether solvent such as diethyl ether, 1,4-dioxane, tetrahydrofuran, 1,2-dimethoxyethane and a hydrocarbon solvent such as pentane, hexane, heptane. The reaction is generally performed at a temperature in the range of $-10°$ C. to $10°$ C. The subsequent hydrolysis is easily conducted by adding water containing trimethylamine, triethylamine or pyridine to the reaction solution containing dichlorophosphate.

If desired, (S)-2,3-dihydropolyprenyl monophosphates as produced above can be converted to their pharmaceutically acceptable salts which are included within the scope of the present invention. For instance, there are mentioned potassium, sodium, calcium and ammonium salts of (S)-2,3-dihydropolyprenyl monophosphates.

(S)-2,3-Dihydropolyprenols of formula (I) and (S)-2,3-dihydropolyprenyl monophosphates of formula (II) exhibit very potent inhibitory activities against the growth and metastasis of cancers at a low dose in which the corresponding known ($\pm$)-2,3-dihydropolyprenol compounds do not exhibit the effectiveness, which will be shown by the animal experiments in the following examples.

Thus the present invention provides in further aspects agents for inhibiting the growth and/or metastasis of cancers which comprise as an active ingredient a (S)-2,3dihydropolyprenol of formula (I)

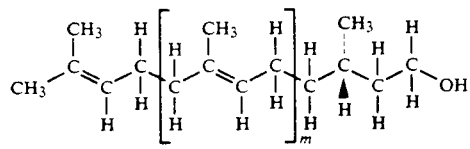

wherein is 7 or 8 or (S)-2 3-dihydropolyprenyl monophosphate of formula (II)

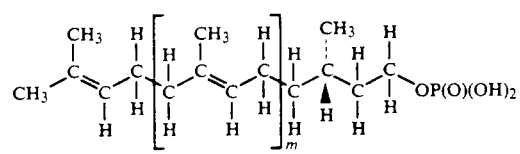

wherein m is 7 or 8 or pharmaceutically acceptable salts thereof.

It is presumed that (S)-2,3-dihydropolyprenols and (S)-2,3-dihydropolyprenyl monophosphates of the present invention can alter a cell surface oligosaccharide structure when one or more are added to the culture system of animal cell and the inhibitory activities against the growth and metastasis of cancers are produced through an influence on such cell surface oligosaccharide structure. This functional mechanism of (S)-2,3-dihydropolyprenols and -dihydropolyprenol monophosphates on the inhibitory activities against the growth and metastasis of cancers is hypothesis and such activities may be produced by another mechanism of those compounds.

On the other hand, it was found surprisingly as shown in the following examples that (R)-2,3-dihydropolyprenol compounds, one of the optical isomers constituting ($\pm$)-2,3-dihydropolyprenol compounds, i.e. the compounds of the following formulas (I') and (II') possess functions of promoting the growth and metastasis of cancers.

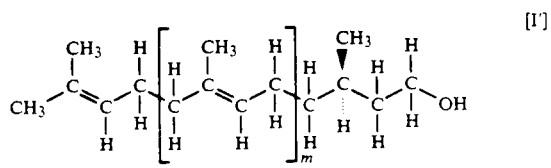

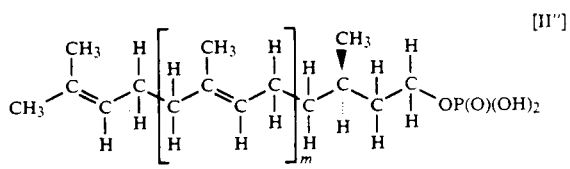

in which m is 7 or 8. One of the reasons why (S)-2,3-dihydropolyprenols and -dihydropolyprenyl monophosphates exhibit more potent inhibitory activities against the growth and metastasis of cancers than the corresponding ($\pm$)-2,3-dihydropolyprenol compounds is thought to be the fact that the influence by (R)-2,3-dihydropolyprenol compounds having opposite function was removed.

The toxicity of (S)-2,3-dihydropolyprenols and -dihydropolyprenyl monophosphates is extremely low. For instance, the acute toxicity test in mice on all of those compounds shows that they have $LD_{50}$ of more than 2 g/kg when administered intraperitoneally to mice.

(S)-2,3-Dihydropolyprenols and -dihydropolyprenyl monophosphates of the present invention are useful for inhibiting the growth and/or metastasis of various kinds of malignant tumors, carcinomas or cancers such as stomach cancer, lung cancer, esophageal cancer, small intestinal cancer, large intestinal cancer, rectal cancer, uterine cancer, bladder cancer, skin cancer, melanoma, heptoma, pancreatoma, breast cancer, encephalophyma, lymphoma, etc.

The active ingredients, i.e., said (S)-2,3-polyprenols and polyprenyl monophosphates can usually be administered orally or parenterally, e.g. subcutaneously or intravenously, in the form of various pharmaceutical preparations such as tablets, capsules, powders, granules, injections, emulsions, suspensions, etc. In the formulation of the pharmaceutical preparations, conventional additives may be used such as vehicles, stabilizers, antimicrobial preservatives, solubilizers, wetting agents, emulsifiers, lubricants, sweetening agents, colorants, flavoring agents, tonicity agents, buffering agents, antioxidants and the like.

The dosage administered will vary depending upon a mode and route of administration, kind of cancers, age, sex and weight of patients, nature and extent of symptoms, kind of concurrent treatment, frequency of treatment, etc. Usually, a daily dose of the active ingredient for adult humans can be about 0.1 to 100 mg or more for oral administration and about 0.01 to 10 mg or more for parenteral administration.

The compounds of the present invention can be used as an agent for the treatment of cancers in the form of a medicament comprising those compounds as a single active ingredient, or they can be used in combination with other known anticancer agents. Alternatively, they can be used in association with surgical treatment, radiotherapy or the like. In any case, the effect of cancer treatment is increased with consequent prolongation of life.

The invention will be further illustrated by the following non-limitative examples.

EXAMPLE 1

(S)-2,3-Dihydrosolanesol (Compound 1) (compound of formula I (m=7))

A solution of solanesol (compound of formula III (m=7)) (15.0 g, 23.8 mmol) in oxygen-free methylene chloride (13.2 ml)/methanol (52.8 ml) was charged into 200 ml autoclave in a stream of argon and Ru((R)-BINAP)(O$_2$CCH$_3$)$_2$ (20.0 mg, 23.8 μmol) was added. The mixture was stirred at a hydrogen pressure of 30 kg/cm$^2$ at room temperature for 22 hrs. After distillating away the solvent, the residue was purified by silica gel chromatography (eluent: 10% ethyl acetate/hexane) to give 14.9 g of the title compound. Specific rotation: $[\alpha]_D^{25} - 1.43°$ (c 5.00, CHCl$_3$) IR spectrum (liquid film method): 3340, 2930, 2860, 1670, 1455, 1390, 1160, 1110, 1065cm$^{-1}$ NMR spectrum (CDCl$_3$): δ0.91(2 H, d, J=6.8 Hz), 1.20(1 H, m), 1.31-1.48(4 H, m), 1.60(24 H, s), 1.63(3 H, s), 1.95-2.10(31 H, m), 3.68(2 H, m), 5.12(8 H, m)

Determination of Optical Purity:

The resultant Compound 1 was converted by Jones oxidation into the carboxylic acid which was then reacted with (S)-(-)-1-(1-naphthyl)ethylamine to form the amide. The separation and analysis of the diastereomer were performed by high performance liquid chromatography (column: Nucleosil 50-5, 4.6×250 mm, solvent: hexane/ethyl acetate (9:1), 1.5 ml/min; detection 254 nm). The peak of the diastereomer derived from (S)-2,3-dihydrosolanesol was detected in about 16 minutes and the peak of the diastereomer derived from (R)-2,3-dihydrosolanesol was detected in about 12 minutes. The optical purity of Compound 1 was found 95.5% e.e.

EXAMPLE 2

(S)-2,3-Dihydrodecaprenol (Compound 2) (compound of formula I (m=8))

The title compound was prepared from decaprenol (compound of formula III (m=8)) in a similar manner to that of Example 1.

m.p. 30° C.

Specific rotation: $[\alpha]_D^{25} - 1.40°$ (c 5.00, CHCl$_3$)

IR spectrum (liquid film method): 3340, 2930, 2860, 1670, 1455, 1390, 1155, 1110, 1065cm$^{-1}$ NMR spectrum (CDCl$_3$):δ0.91(2 H, d, J=6.4 Hz), 1.20(1 H, m), 1.32-1.48(4 H, m), 1.60(27 H, s), 1.68(3 H, s), 1.95-2.17(35 H, m), 3.67(2 H, m), 5.12(9 H, m)

The optical purity was determined similarly to Example 1 to show 96.6% e.e.

EXAMPLE 3

(S)-2,3-Dihydrosolanesyl monophosphate (Compound 3) (compound of formula II (m=7))

A solution of (S)-2,3-dihydrosolanesol (Compound 1:2.50 g, 3.9 mmol) and triethylamine (0.80 ml, 5.9 mmol) in tetrahydrofuran (25 ml) was added dropwise to phosphorus oxychloride (2.6 ml, 27 mmol) over a period of 20 minutes while stirring under ice-cooling. Afterwards, the stirring was continued for 2 hrs. at the same temperature. The reaction solution was concentrated, the residue was mixed with diethyl ether (25 ml) and the mixture was stirred at room temperature for 1.5 hrs. After removal of the insoluble matters, the concentrated residue was dissolved in tetrahydrofuran (25 ml) and the solution was poured into iced water (100 ml) containing triethylamine (10 ml) and stirred for 1 hr. The solution was made acid with 10% hydrochloric acid and extracted with isopropyl ether. The organic phase was washed with water, dried over magnesium sulfate (anhydrous) and concentrated. To the residue were added methanol (80 ml) and octadecylsilane (5 g) and the mixture was stirred at room temperature for 10 minutes. After filtering off octadecylsilane (5 g), the concentrated residue was crystallized from methanol to afford 2.10 g of the title compound.

m.p. 30-31° C.

Specific rotation: $[\alpha]_D^{21} - 1.73°$ (c 5.00, CHCl$_3$)

IR spectrum (KBr tablet method): 3440, 2930, 2860, 1670, 1455, 1390, 1065, 1020cm$^{-1}$ NMR spectrum (CDCl$_3$): δ0.90(3 H, d, J=6.4 Hz), 1.15-1.75(5 H, m), 1.60(24 H, s), 1.68(3 H, m), 1.95-2.11(30 H, m), 3.10(2 H, br), 4.12(2 H, m), 5.11(8 H, m)

EXAMPLE 4

(S)-2,3-Dihydrodecaprenyl monophosphate (Compound 4) (compound of formula II (m=8))

The title compound was prepared from (S) 2,3-dihydrodecaprenol (Compound 2) in a similar manner to that of Example 3.

m.p. 36.5° C.

Specific rotation: $[\alpha]_D^{23} - 1.61°$ (c 5.00, CHCl$_3$)

IR spectrum (KBr tablet method): 3460, 2930, 2860, 1670, 1455, 1390, 1070, 1035cm$^{-1}$ NMR spectrum (CDCl$_3$): δ0.90(3 H, d, J=6.3 Hz), 1.13-1.75(5 H, m), 1.60(27 H, s), 1.68(3 H, s), 1.95-2.10(34 H, m), 4.07(2 H, m), 4.15(2 H, br), 5.12(9 H, m)

REFERENCE EXAMPLE 1

(R)-2,3-Dihydrosolanesol (Compound 7) (compound of formula I' (m=7))

A solution of solanesol (compound of formula III (m=7)) (15.0 g, 23.8 mmol) in oxygen-free methylene chloride (13.2 ml)/methanol (52.8 ml) was charged into 200 ml autoclave in a stream of argon and Ru((S)-BINAP)(O$_2$CCH$_3$)$_2$ (20.0 mg, 23.8 μmol) was added. The mixture was stirred at a hydrogen pressure of 30 kg/cm$^2$ at room temperature for 22 hrs. After distilling away the solvent, the residue was purified by silica gel chromatography (eluent: 10% ethyl acetate/hexane) to give 14.9 g of the title compound.

Specific rotation: $[\alpha]_D^{25} + 1.43°$ (c 5.00, CHCl$_3$)

IR spectrum (liquid film method): 3340, 2930, 2860, 1670, 1455, 1390, 1160, 1110, 1065cm$^{-1}$ NMR spectrum (CDCl$_3$): δ0.91(2 H, d, J=6.8 Hz), 1.20(1 H, m), 1.31–1.48(4 H, m), 1.60(24 H, s), 1.63(3 H, s), 1.95–2.10(31 H, m), 3.68(2 H, m), 5.12(8 H, m)

Determination of Optical Purity:

The resultant Compound 1 was converted by Jones oxidation into the carboxylic acid which was then reacted with (S)-(-)-1-(1-naphthyl)ethylamine to form the amide. The separation and analysis of the diastereomer were performed by high performance liquid chromatography (column: Nucleosil 50-5, 4.6×250 mm, solvent: hexane/ethyl acetate (9:1), 1.5 ml/min; detection 254 nm). The peak of the diastereomer derived from (S)-2,3-dihydrosolanesol was detected in about 16 minutes and the peak of the diastereomer derived from (R)-2,3-dihydrosolanesol was detected in about 12 minutes. The optical purity of Compound 7 was found 93.8% e.e.

REFERENCE EXAMPLE 2

(R)-2,3-Dihydrodecaprenol (Compound 8) (compound of formula I' (m=8))

The title compound was prepared from decaprenol (compound of formula III (m=8)) in a similar manner to that of Reference Example 1.

m.p. 30° C.

Specific rotation: $[\alpha]_D^{25}+1.42°$ (c 5.00, CHCl$_3$)

IR spectrum (liquid film method): 3340, 2930, 2860, 1670, 1455, 1390, 1155, 1110, 1065cm$^{-1}$ NMR spectrum (CDCl$_3$): δ0.91(2 H, d, J=6.4 Hz), 1.20(1 H, m), 1.32–1.48(4 H, m), 1.60(27 H, s), 1.68(3 H, s), 1.95–2.17(35 H, m), 3.67(2 H, m), 5.12(9 H, m)

The optical purity was determined similarly to Example 1 to show 93.0% e.e.

REFERENCE EXAMPLE 3

(R)-2,3-Dihydrosolanesyl monophosphate (Compound 9) (compound of formula II' (m=7))

A solution of (R)-2,3-dihydrosolanesol (Compound 7: 2.50 g, 3.9 mmol) and triethylamine (0.80 ml, 5.9 mmol) in tetrahydrofuran (25 ml) was added dropwise to phosphorus oxychloride (2.6 ml, 27 mmol) while stirring under ice-cooling in 20 minutes. Afterwards, the stirring was continued for 2 hrs. at the same temperature. The reaction solution was concentrated, the residue was mixed with diethyl ether (25 ml) and the mixture was stirred at room temperature for 1.5 hrs. After removal of the insoluble matters, the concentrated residue was dissolved in tetrahydrofuran (25 ml) and the solution was poured into iced water (100 ml) containing triethylamine (10 ml) and stirred for 1 hr. The solution was made acid with 10% hydrochloric acid and extracted with isopropyl ether. The organic phase was washed with water, dried over magnesium sulfate (anhydrous) and concentrated. To the residue were added methanol (80 ml) and octadecylsilane (5g) and the mixture was stirred at room temperature for 10 minutes. After filtering off octadecylsilane (5 g), the concentrated residue was crystallized from methanol to afford 2.24 g of the title compound.

m.p. 30°–31° C.

Specific rotation: $[\alpha]_D^{21}+1.65°$ (c 5.00, CHCl$_3$)

IR spectrum (KBr tablet method): 3440, 2930, 2860, 1670, 1455, 1390, 1065, 1020cm$^{-1}$ NMR spectrum (CDCl$_3$): δ0.90(3 H, d, J=6.4 Hz), 1.15–1.75(5 H, m), 1.60(24 H, s), 1.68(3 H, m), 1.95–2.11(30 H, m), 3.10(2 H, br), 4.12(2 H, m), 5.11(8 H, m)

REFERENCE EXAMPLE 4

(R)-2,3-Dihydrodecaprenyl monophosphate (Compound 10) (compound of formula II' (m=8))

The title compound was prepared from (R)-2,3-dihydrodecaprenol (Compound 2) in a similar manner to that of Reference Example 3.

m.p. 36.5° C.

Specific rotation: $[\alpha]_D^{23}+1.62°$ (c 5.00, CHCl$_3$)

IR spectrum (KBr tablet method): 3460, 2930, 2860, 1670, 1455, 1390, 1070, 1035cm$^{-1}$ NMR spectrum (CDCl$_3$): δ0.90(3 H, d, J=6.3 Hz), 1.13–1.75(5 H, m), 1.60(27 H, s), 1.68(3 H, s), 1.95–2.10(34 H, m), 4.07(2 H, m), 4.15(2 H, br), 5.12(9 H, m)

EXAMPLE 5

Compounds 2 and 4 of the present invention as well as (±)-2,3-dihydrodecaprenol (Compound 5) and (±)-2,3-dihydrodecaprenyl monophosphate (Compound 6) of the prior art were tested for the inhibitory effects of those compounds on the pulmonary metastasis of intravenously transplanted tumor cell in mouse.

Test animal: male C57BL/6 mice (6 weeks old)

Tumor cell: Highly metastatic melanoma cell, B16-F10

Test method: 8×10$^4$ B16-F10 melanoma cells were transplanted into the tail vein of mice. An oily emulsion containing Compound 2, 4, 5 or 6 was administered to the tail vein for three times, the day before the transplantation, the day of transplantation and the day after the transplantation. The oily emulsion comprises 10% soybean oil, 1.2% soybean lecithin, 2.5% glycerol and a suitable amount of Compound 2, 4, 5 or 6. To control mice were administered an oily emulsion free from the compound. On day 14 after transplantation, the mice were sacrificed and the number of metastatic nodules formed on the lung surface was counted for each mouse. 9 to 13 animals were used per each group. Inhibition of metastasis (%) was calculated on the basis of the following formula.

TABLE 1

| Compound | Dose (μg/kg) | Number of metastatic nodules Mean ± Standard error | % relative to control |
|---|---|---|---|
| Control |  | 94 ± 13 | 100 |
| 4 | 0.3 | 55 ± 11 | 59 |
| 4 | 1.0 | 53 ± 20 | 56 |
| 4 | 3.0 | 78 ± 32 | 83 |
| 2 | 1.0 | 60 ± 14 | 64 |
| 6 | 1.0 | 91 ± 13 | 97 |
| 5 | 1.0 | 110 ± 34 | 117 |

The data in Table 1 show that (S)-2,3-dihydropolyprenol compounds 4 and 2 of the present invention significantly inhibit the pulmonary metastasis of the intravenously transplanted tumor cell at the dose which (±)-2,3-dihydropolyprenol compounds 6 and 5 of the prior art do not exhibit the efficacy.

EXAMPLE 6

Compounds 2, 4, 5 and 6 of the present invention as well as (R)-2,3-dihydrodecaprenyl monophosphate (Compound 10) of the prior art were tested for the inhibitory effects of those compounds on the pulmonary metastasis of the tumor formed in the foot pad of mouse.

The animal and tumor cell used were the same as those used in Example 5. Test method: 4×10$^5$ B16-F10 melanoma cells were transplanted into the foot pad of the left hind leg of mice. Mice were allowed to stand for 14 days after transplantation to form the tumor in the transplanted region. An oily emulsion containing Compound 2, 4, 5, 6 or 10 was subcutaneously administered seven times to the right flank of mice every other day from day 15 to day 27 after transplantation. The left hind leg was resected on day 28 after transplantation, the mice were sacrificed on day 42 and the number of metastatic nodules formed on the lung surface was counted for each mouse. 10 to 14 animals were used per each group.

TABLE 2

| Compound | Dose (μg/kg) | Number of metastatic nodules Mean ± Standard error | % relative to control |
| --- | --- | --- | --- |
| Control |  | 23.9 ± 10.5 | 100 |
| 4 | 0.5 | 10.5 ± 5.6 | 44 |
| 4 | 2.5 | 1.1 ± 0.6 | 5 |
| 2 | 2.5 | 6.3 ± 3.2 | 26 |
| 6 | 2.5 | 24.2 ± 8.7 | 101 |
| 5 | 2.5 | 22.1 ± 9.8 | 92 |
| 10 | 2.5 | 35.4 ± 14.6 | 148 |

The data in Table 2 show that (S)-2,3-dihydropolyprenol compounds 4 and 2 of the present invention remarkably inhibit the pulmonary metastasis of the tumor formed in the foot pad at the dose which (±)-2,3-dihydropolyprenol compounds 6 and 5 of the prior art do not exhibit the efficacy. (R)-2,3-Dihydropolyprenol compound 10 exhibit the efficacy. (R)-2,3-Dihydropolyprenol compound 10 accelerated the pulmonary metastasis of the tumor contrary to the corresponding (S)-2,3-dihydropolyprenol compound 4.

EXAMPLE 7

Compound 4 of the present invention was tested for the inhibitory effect on the lymph node metastasis of the human lung carcinoma cell-derived tumor formed in the femur of nude mouse.

Test animal: male KSN nude mice (5 weeks old)
Tumor cell: Human lung carcinoma cell, AOI
Test method: $2 \times 10^5$ AOI carcinoma cells were intradermally transplanted into the right femur of nude mice. When an average diameter of the tumor formed in the transplanted region reached about 9.5 mm, subcutaneous administration (three times per week) of an oily emulsion containing Compound 4 was started. After an administration period of five weeks, the mice were sacrificed and the incidence of metastasis in the right inguinal lymph node was examined. 13 animals were used per each group.

TABLE 3

| Compound | Dose (μg/kg) | Incidence of lymph node metastasis |
| --- | --- | --- |
| Control |  | 13/13 (100%) |
| 4 | 0.1 | 12/13 (92%) |
| 4 | 0.5 | 9/13 (69%) |

The data in Table 3 show that (S)-2,3-dihydropolyprenyl compound 4 of the present invention inhibits the lymph node metastasis of the human lung carcinoma cell-derived tumor formed in the femur of nude mouse.

EXAMPLE 8

Compounds 4, 6 and 10 of the present invention were tested for the effects of those compounds on an antitumor activity of a mouse immune system.

The animal and tumor cell used were the same as those used in Example 5.

Test method: An oily emulsion containing Compound 4, 6 or 10 was intraperitoneally administered to mice seven times every other day. The day after the final administration, $5 \times 10^4$ B16-F10 melanoma cells were subcutaneously transplanted into the right frank of mice. On day 11 after transplantation, an average diameter of the tumor formed in the transplanted region [(longest diameter+shortest diameter)×½] was measured. 10 to 15 animals were used per each group.

TABLE 4

| Compound | Dose (μg/kg) | Average diameter of tumor (mm) Mean ± Standard error | % relative to control |
| --- | --- | --- | --- |
| Control |  | 6.0 ± 0.7 | 100 |
| 4 | 300 | 3.2 ± 1.3 | 53 |
| 6 | 300 | 4.7 ± 0.5 | 78 |
| 10 | 300 | 8.8 ± 0.4 | 147 |
| 4 | 50 | 3.5 ± 1.1 | 58 |
| 6 | 50 | 6.1 ± 0.3 | 102 |

The data in Table 4 show that (S)-2,3-dihydropolyprenol compound 4 of the present invention enhances an antitumor activity of the mouse immune system and exhibits a significant effect of inhibiting the tumor growth at the dose which the corresponding (±)-2,3-dihydropolyprenol compound 6 does not exhibit the efficacy. (R)-2,3-Dihydropolyprenol compound 10 reduced the antitumor activity of the mouse immune system and accelerated the tumor growth contrary to the corresponding (S)-2,3-dihydropolyprenol compound 4.

The following examples illustrate representative pharmaceutical preparations of the present compounds.

Soft capsules for oral administration (S)-2,3-Dihydrodecaprenyl monophosphate 4 (50 g) and polyethylene glycol (Macrogoal 400) (130 g) were mixed to form a uniform solution. Separately, a gelatin solution was prepared which comprises gelatin (93 g), glycerol (19 g), D-sorbitol (10 g), ethyl para-hydroxybenzoate (0.4 g), propyl para-hydroxybenzoate (0.2 g) and titanium oxide (0.4 g). The gelatin solution was used as a capsule coating agent to form a soft capsule containing 190 mg of the contents according to a manually operated flat plate punching process.

Injections

Soybean oil (50 g), soybean lecithin (6 g), glycerol (12.5 g) and (S)-2,3-dihydrodecaprenyl monophosphate 4 (2.5 g) were mixed and the mixture was dissolved by heating to 50°-60° C., to which was added distilled water (250 ml). The solution was homogenized with a mixer to form a crude emulsion. Distilled water was added to the crude emulsion to make up a total amount of 500 ml. The crude emulsion was charged into a Manton-Gaulin type high pressure tank for emulsion and circulated to prepare a homogeneous oily emulsion. The oily emulsion was dispensed to 1 cc of an ampule under sterile conditions and the ampule was melt-closed.

What is claimed is:

1. A (S)-2,3-dihydropolyprenyl monophosphate of formula (II)
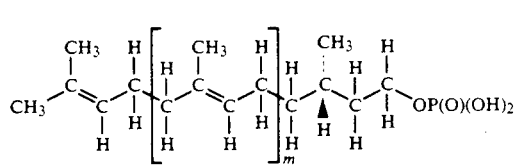
wherein m is 7 or 8 or the pharmaceutically acceptable salt thereof.
2. An agent for inhibiting the growth and/or metastasis of cancers which comprises as an active ingredient, a (S)-2,3-dihhydropolyprenyl monophosphate of formula (II)
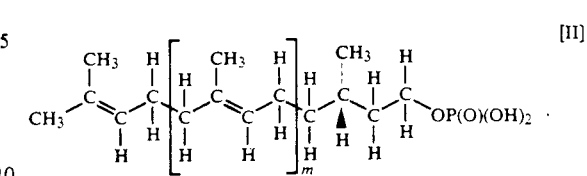
wherein m is 7 or 8 or the pharmaceutically acceptable salt thereof.
* * * * *

UNITED STATES PATENT AND TRADEMARK OFFICE
CERTIFICATE OF CORRECTION

PATENT NO. : 5,306,714
DATED     : APRIL 26, 1994
INVENTOR(S) : YASUSHI OKAMOTO ET AL

It is certified that error appears in the above-indentified patent and that said Letters Patent is hereby corrected as shown below:

Column 3, line 53, "(S)-2 3-dihydropolyprenyl" should read --(S)-2,3-dihydropolyprenyl--.

Column 12, line 1, "(S)-2,3-dihhydropolyprenyl" should read --(S)-2,3-dihydropolyprenyl--.

Signed and Sealed this

Twenty-third Day of August, 1994

Attest:

BRUCE LEHMAN

*Attesting Officer*    *Commissioner of Patents and Trademarks*